United States Patent [19]

Marsili et al.

[11] 4,327,096
[45] Apr. 27, 1982

[54] 3-AMIDINO ANSAMYCINS

[75] Inventors: Leonardo Marsili; Giovanni Franceschi; Aurora Sanfilippo, all of Milan, Italy

[73] Assignee: Farmitalia Carlo Erba S.p.A., Milan, Italy

[21] Appl. No.: 232,533

[22] Filed: Feb. 9, 1981

[51] Int. Cl.³ .................. A61K 31/395; C07D 498/08
[52] U.S. Cl. .............................. 424/250; 424/248.54; 424/258; 424/244; 260/239.3 P
[58] Field of Search .................. 260/239.3 P; 424/244, 424/248.54, 250, 258

[56] References Cited

U.S. PATENT DOCUMENTS 4,124,585 11/1978 Mars et al. .................. 260/239.3 P Primary Examiner—Robert T. Bond
Attorney, Agent, or Firm—Oblon, Fisher, Spivak, McClelland & Maier

[57] ABSTRACT

Novel 3-amidino rifamycins having the formula:

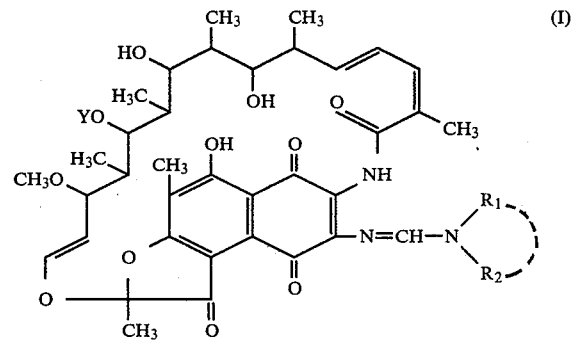

wherein Y is —H or —COCH$_3$; R$_1$ and R$_2$ may be linear or branched alkyl having from 1 to 7 carbon atoms and alkenyl having 3 or 4 atoms and R$_2$ may be also chloroalkyl having from 2 to 4 carbon atoms, cycloalkyl having from 3 to 7 carbon atoms in the ring, cycloalkylalkyl having from 3 to 6 carbon atoms in the ring, phenyl, bornyl, arylalkyl hydrocarbon having 7 or 8 carbon atoms which may be substituted with one halogen atom in the aryl group; and R$_1$ and R$_2$ along with the N atom to which they are bonded form an unsubstituted cyclic moiety having from 5 to 8 carbon atoms, a cyclic moiety having from 5 to 8 carbon atoms substituted with 1 or 2 methyl radicals, 4-alkylpiperazine, morpholine, 1,2,3,4-tetrahydroisoquinoline.

These novel compounds are from grey to dark solids having high antibacterial activity which are obtained by reacting 3-amino rifamycin S or SV with a chloroformiminio chloride.

12 Claims, No Drawings

3-AMIDINO ANSAMYCINS

This invention relates to novel 3-amidino rifamycins and more particularly to S and SV rifamycin derivatives having antibiotic activity, to methods for their preparation and to pharmaceutical compositions and preparations comprising them. The novel rifamycin compounds have the formula

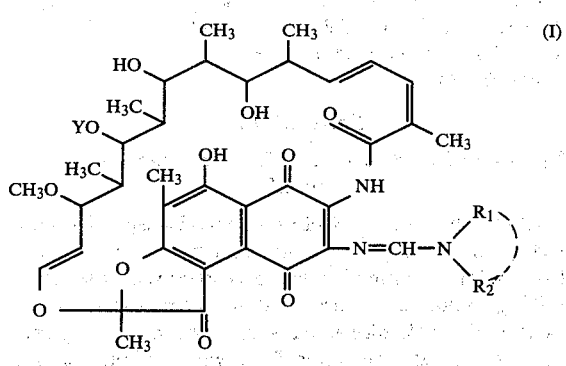

wherein: Y is —H or —COCH$_3$; R$_1$ is selected from the group consisting of linear or branched alkyl having 1 to 7 carbon atoms, and alkenyl having 3 or 4 carbon atoms; R$_2$ is selected from the group consisting of linear or branched alkyl having from 1 to 7 carbon atoms, chloroalkyl having from 2 to 4 carbon atoms, alkenyl having 3 or 4 carbon atoms, cycloalkyl having from 3 to 7 carbon atoms in the ring, cycloalkyl alkyl having from 3 to 6 carbon atoms in the ring, phenyl, bornyl, unsubstituted arylalkyl hydrocarbon having 7 or 8 carbon atoms, arylalkyl hydrocarbon having 7 or 8 carbon atoms and substituted with one halogen atom in the aryl group; and R$_1$ and R$_2$ along with the N atom to which they are bonded form an unsubstituted cyclic moiety having from 5 to 8 carbon atoms, a cyclic moiety having from 5 to 8 carbon atoms substituted with 1 or 2 methyl radicals, 4-alkylpiperazine, morpholine, 1,2,3,4-tetrahydroisoquinoline.

The invention relates also to compounds which are obtained by reduction of the compounds of formula (I), having the formula:

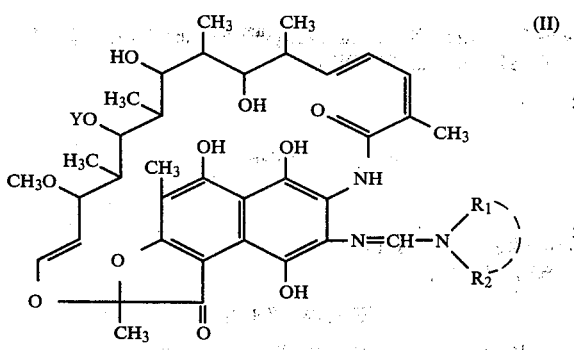

wherein Y, R$_1$ and R$_2$ are as above defined.

The rifamycin compounds according to the present invention have antibacterial activity against Gram-positive and Gram-negative bacteria and against *Mycobacterium tuberculosis*.

The compounds of formula (I) are from grey to dark solids, while those of formula (II) are orange solids. They are generally soluble in most organic solvents, such as chlorinated solvents, alcohols and esters. The compounds of formula (I) are insoluble in aqueous solutions but soluble in aromatic hydrocarbons, whereas the compounds of formula (II) are slightly soluble in water at a pH between 7 and 8.

The compounds of formula (I) are obtained by reaction of 3-amino rifamycin S of formula:

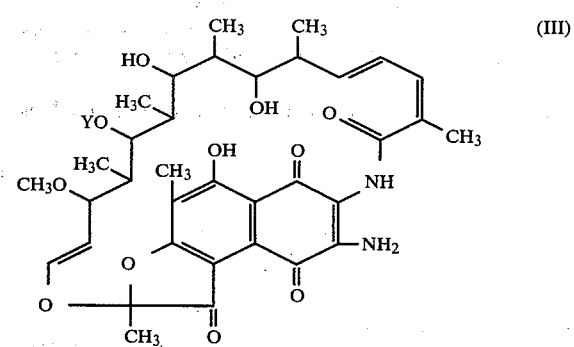

wherein Y is —H or —COCH$_3$, in the presence of a tertiary amine and of an aprotic solvent, with a chloroformiminio chloride of formula

wherein R$_1$ and R$_2$ are as above defined.

Following the same reaction but making use of the 3-amino rifamycin SV in the place of the 3-amino rifamycin S, the reduced compounds of formula (II) are directly obtained.

The compounds of formula (III) are disclosed in the German Pat. No. 1670377 and in the U.S. Pat. No. 4,007,169. The compounds of formula (IV) are described in the British Pat. No. 1,293,590 and in the corresponding French Pat. No. 2073338 and German Pat. No. 2055531.

The rifamycin compounds according to the present invention can be formulated in conventional ways, as will be apparent to those skilled in the art. Thus, they can be used in conjunction with a pharmaceutically-accepted carrier or diluent. The compounds, whether or not in conjunction with a carrier or diluent, can be formulated for administration in conventional unit dosage forms.

The C atoms in the PMR spectra are numbered according to IUPAC rules.

The invention is illustrated by the following Examples of compounds and method of preparing the same.

EXAMPLE 1

3-[(Hexahydro-1H-azepin-1-yl)methylenamino]rifamycin S 16 g 3-amino-rifamycin S are dissolved in 150 ml CHCl$_3$ and 2,5 ml triethylamine are added to the solution.

After cooling at −30° C., 9.5 chlorohexahydroazepinylformiminio chloride dissolved in 150 ml CHCl$_3$ are added dropwise under stirring.

The solution is gently warmed up to 20° C., washed with water and dried with sodium sulphate. After filtering, the solvent is evaporated under vacuum, the residue is dissolved in 100 ml dichloromethane, the solution is diluted with 300 ml cyclohexane and then concentrated to 250 ml under vacuum.

The precipitate is filtered, the solvent is evaporated under vacuum, the residue is dissolved in 100 ml ethyl ether, the solution is diluted with 200 ml petroleum ether, washed with a phosphate buffer solution at pH 7.5 and then with water. The organic phase is dried with sodium sulphate, filtered and evaporated to dryness.

Yield: 1.5 g of compound of formula (I) wherein Y is —COCH₃ and

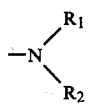

is hexahydroazepinyl.

P.M.R. (CDCl₃): 0.43 δ[d, CH₃—C(22)]; 0.77 δ[d, CH₃—C(20)] 0.87 δ[d, CH₃—C(16)]; 1.07 δ[d, CH₃—C(18)]; 1.80 δ[s, CH₃—C(2)]; 2.03 δ[s,CH₃COO—C(21)]; 2.13 δ[s, CH₃—C(12)]; 2.30 δ[s, CH₃—C(4)]; 3.15 δ[s, CH₃O—];

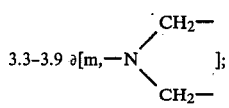

4.5–5.4 δ[m, C(21)H and C(24)H]; 5.8–6.8 δ[m, C(13)H, C(14)H, C(15)H; C(25)H]; 7.40 δ[bs, NH—CO]; 8.12 δ[s, N=CH—N]

MS: 819 (M+)

EXAMPLE 2

3-[(Piperidin-1-yl)methylenamino]rifamycin S 8 g 3-amino-rifamycin S are dissolved in 100 ml dichlorometane, 7 ml triethylamine are added and the solution is cooled at −40° C. A solution of 8 g chloropiperidylformiminio chloride in 50 ml dichloromethane is dropwise added and the temperature is kept at −40° C. for 60 minutes. The solution is gently warmed up to room temperature, washed with diluted acetic acid and then with water. After drying with sodium sulphate, the solution is evaporated under vacuum and the residue is extracted with 400 ml ethyl ether. The ethereal solution is washed with a phosphate buffer solution at pH 7.5 and then with water.

After drying with sodium sulphate the solution is diluted with 100 ml petroleum ether and then concentrated to 50 ml under vacuum. The precipitate is filtered yielding 2 g of a compound of formula (I) wherein Y is —COCH₃ and

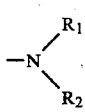

is piperidyl.

P.M.R. (CDCl₃): 0.43 δ[d, CH₃—C(22)]; 0.68 δ[d,CH₃—C(20)]; 0.79 δ[d,CH₃—C(16)]; 0.97 δ[d, CH₃—C(18)]; 1.75 δ[s,CH₃—C(2)]; 1.98 δ[s, CH₃COO—C(21)]; 2.08s δ[s, CH₃—C(12)]; 2.27 δ[s,CH₃—C(4)]; 3.14 δ[s,CH₃O—];

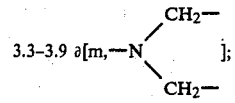

4.7–5.3 δ[m,C(21)H and C(24)H]; 5.5–6.7 δ[m, C(13)H,C(14)H, C(15)H and C(25)H]; 7.67 δ[bs, NH—CO]; 8.20 [s,N=CH—N]

MS: 805 (M+)

EXAMPLE 3

3-[(Hexahydro-1H-azepin-1-yl)methylenamino]rifamycin SV 0.250 g of 3-[(hexahydro-1H-azepin-1-yl)methylenamino]rifamycin S obtained in example 1 are dissolved in 10 ml methanol and reacted with a solution of 0.5 g sodium ascorbate in 10 ml water. After stirring for 20′ 30 ml dichlorometane are added, the organic phase is washed with water, dried with sodium sulphate and filtered. The solvent is evaporated under vacuum, the residue is treated with petroleum ether and the precipitate is filtered. 0.200 g of a compound of formula (II) are obtained, wherein Y is —COCH₃ and

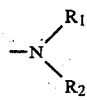

is hexahydroazepinyl.

P.M.R. (CDCl₃): −0.09 δ[d, CH₃—C(22)]; 0.48 δ[d,CH₃—C(20)]; 0.83 δ[d,CH₃—C(16)]; 1.01 δ[d, CH₃—C(18)]; 1.77 δ[s,CH₃—C(2)]; 1.97 δ[s, CH₃COO—C(21)]; 2.03 δ[s,CH₃—C(12)]; 2.10 δ[s,CH₃—C(4)]; 3.04 δ[s,CH₃O—];

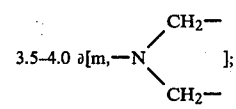

4.7–5.6 δ[m,C(21)H and C(24)H]; 6.0–6.5 δ[m, C(13)H, C(14)H, C(15)H, C(25)H];

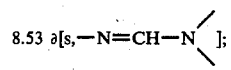

8.63 δ[bs, N H—CO].

MS: 821 (M+)

EXAMPLE 4

3-[(Pyrrolidin-1-yl)-methylenamino]rifamycin SV 8 g 3-amino-rifamycin S are dissolved in 40 ml tetrahydrofuran and 10 ml triethylamine are added. 7.5 g chloropyrrolidinylformiminio chloride are added at 15° C. The solution is stirred for 20′ at room temperature, 100 ml chloroform are added and the resulting solution is washed with diluted acetic acid and then with water. After drying with sodium sulphate, the solution is filtered and evaporated under vacuum.

The residue is dissolved in 50 ml methanol and reacted with a solution of 1 g sodium ascorbate in 20 ml water. After stirring for 10', 100 ml chloroform are added, the organic phase is washed with water, dried with sodium sulphate and filtered. The solvent is evaporated under vacuum. The residue is stirred with 200 ml ethyl ether for 15'. After filtering, the ethereal solution is extracted with a phosphate buffer solution at pH 7.5. The aqueous phase is washed with ethyl ether, acetic acid is added to pH 3.5 and the aqueous solution is extracted with chloroform. The chloroform phase, washed with water and dried with sodium sulphate, is filtered and diluted with two volumes of petroleum ether. 0.500 g of an orange compound of formula (II) are obtained, wherein Y is —COCH$_3$ and

is pyrrolidinyl.

P.M.R. (CDCl$_3$) −0.05 δ[d, CH$_3$—C(22)]; 0,54 δ[d, CH$_3$—C(20)]; 0.82 δ[d,CH$_3$—C(16)]; 1.04 δ[d,CH$_3$—C(18)]; 1.76 δ[s,CH$_3$—C(2)]; 1.97 δ[s,CH$_3$—COO—C(21)]; 2.07 δ[s,CH$_3$—C(12)]; 2.15 δ[s,CH$_3$—C(4)]; 3.05 δ[s, CH$_3$O-];

3.77 ∂[bs, —N(CH$_2$—)(CH$_2$—)]

4.8–5.5 δ[m,C(21)H and C(24)H]; 6.0–6.5 [m,C(13)H,C(14)H, C(15)H,C(25)H];

8.74 ∂[s,—N=CH—N⟨ ];

8.83 δ[bs, —NH—CO—].
MS: 793 (M+)

EXAMPLE 5

3-[(4methyl-piperazin-1-yl)methylenamino]rifamicin SV

Following the same procedure of example 4 and reacting 3-amino-rifamycin S with chloro-(4-methyl-piperazin-1-yl)formiminio chloride a compound of formula (II) is obtained wherein Y is —COCH$_3$ and

is 4-methyl-piperazinyl.
MS: 822 (M+)

The activity in vitro of the novel rifamycin compound obtained according to the foregoing Example 4 has been tested by serial twofold dilution technique in solid medium (Gram+ and Gram−bacteria) or in liquid medium (Mycobacterium tuberculosis).

After incubation at 37° C. the MICS were recorded as the minimal concentrations able to prevent any visible growth of the test strains.

The results, in comparison with those of Rifampicin, are set out in the following table, wherein the figures are the values of the minimal inhibiting concentration (MIC) given in mcg/ml.

| Strains | Ex. 4 | Rifampicin |
| --- | --- | --- |
| Staphylococcus aureus | 0.0045 | 0.009 |
| Streptococcus feacalis | 1.25 | 0.3 |
| Streptococcus pyogenes | 0.6 | 0.6 |
| Sarcina lutea | 0.0045 | 0.009 |
| Mycobacterium tuberculosis | 0.0025 | 0.01 |
| Escherichia coli | 200 | 10 |
| Klebsiella pneumoniae | 200 | 5 |
| Proteus vulgaris | 2.5 | 2.5 |
| Pseudomonas aeruginosa | 200 | 10 |
| Salmonella abortivoequina | 200 | 2.5 |

Compound of example 4 inhibits the growth of Gram positive bacteria and Mycobacterium tuberculosis at very low concentrations. The inhibitory action against Mycobacterium tuberculosis is noteworthy, since it is 4 times higher than that of Rifampicin. The spectrum of activity of the compound of example 4 is more limited than that of Rifampicin; in fact some Gram-negative strains are insensitive to the new compound.

What we claim is:
1. A 3-amidino rifamycin having the formula

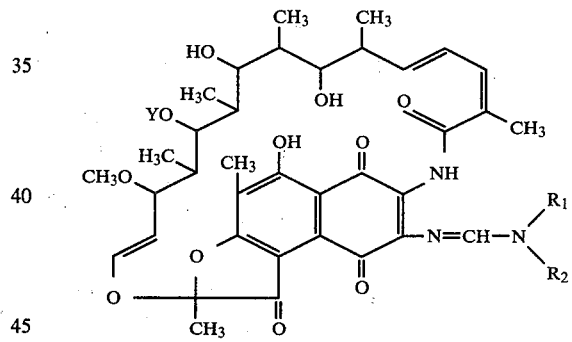

Wherein: Y is —H or —COCH$_3$; R$_1$ is selected from the group consisting of linear or branched alkyl having from 1 to 7 carbon atoms, and alkenyl having 3 or 4 carbon atoms; R$_2$ is selected from the group consisting of linear or branched alkyl having from 1 to 7 carbon atoms, chloroalkyl having from 2 to 4 carbon atoms, alkenyl having 3 or 4 carbon atoms, cycloalkyl having from 3 to 7 carbon atoms in the ring, cycloalkylalkyl having from 3 to 6 carbon atoms in the ring, phenyl, bornyl, unsubstituted arylalkyl hydrocarbon having 7 or 8 carbon atoms, arylalkyl hydrocarbon having 7 or 8 carbon atoms and substituted with one halogen atom in the aryl group; and R$_1$ and R$_2$ along with the N atom to which they are bonded form a cyclic moiety, said moiety being pyrrolidinyl, piperidinyl, hexahydroazepinyl, or heptahydroazocinyl, each of which may be unsubstituted or substituted with 1 or 2 methyl radicals, 4-alkyl-piperazinyl, morpholinyl, or 1,2,3,4-tetrahydroisoquinolinyl.

2. A reduced compound of formula (I) having the formula (II) [structure of rifamycin compound with substituents Y, R₁, R₂, showing —N=CH—NR₁R₂ group]

wherein Y, R₁ and R₂ are as defined in claim 1.

3. Method of preparing a rifamycin compound of formula (I) according to claim 1, characterized in that a compound of formula

[structure of rifamycin compound with —NH₂ group]

wherein Y is —H or —COCH₃ is reacted, in the presence of a tertiary amine and of an aprotic solvent, with a chloroformiminio chloride of formula $$\begin{array}{c} R_1 \\ \diagdown \\ N^+ \\ \diagup \\ R_2 \end{array} \begin{array}{c} CHCl \\ \| \\ \\ Cl^- \end{array} \quad (IV)$$

wherein R₁ and R₂ are as defined in claim 1.

4. Method according to claim 3, characterized in that said tertiary amine is triethylamine.

5. Method according to claims 3 and 4, characterized in that said aprotic solvent is selected from the group consisting of tetrahydrofuran and dioxane.

6. Method according to claims 3 and 4, characterized in that said aprotic solvent is selected from the group consisting of methylene chloride, benzene and toluene.

7. The compound of claim 1 wherein Y is —COCH₃ and $$-N\begin{array}{c} R_1 \\ \diagdown \\ \diagup \\ R_2 \end{array}$$

is hexahydroazepinyl.

8. The compound of claim 1 wherein Y is —COCH₃ and $$-N\begin{array}{c} R_1 \\ \diagdown \\ \diagup \\ R_2 \end{array}$$

is piperidyl.

9. The compound of claim 1 wherein Y is —COCH₃ and $$N\begin{array}{c} R_1 \\ \diagdown \\ \diagup \\ R_2 \end{array}$$

is pyrrolidinyl.

10. The compound of claim 1 wherein Y is —COCH₃ and $$N\begin{array}{c} R_1 \\ \diagdown \\ \diagup \\ R_2 \end{array}$$

is 4-methyl-piperazinyl.

11. An antibacterial composition which comprises a rifamycin compound as claimed in claims 1 and 2, and effective amount of an antibacterial acceptable carrier or diluent therefor.

12. A antibacterial preparation which comprises a rifamycin compound as claimed in claims 1 and 2, or an antibacterial composition of claim 11, in unit dosage form.

* * * * *

UNITED STATES PATENT AND TRADEMARK OFFICE
CERTIFICATE OF CORRECTION

PATENT NO. : 4,327,096

DATED : April 27, 1982

INVENTOR(S) : Leonardo Marsili et. al.

It is certified that error appears in the above—identified patent and that said Letters Patent is hereby corrected as shown below:

On the title page insert:

-- [30]  Foreign Application Priority Data

April 12, 1980  [UK]  United Kingdom.....8012168 --

Signed and Sealed this

Twenty-ninth Day of June 1982

[SEAL]

Attest:

GERALD J. MOSSINGHOFF

Attesting Officer  Commissioner of Patents and Trademarks